United States Patent [19]

Juday

[11] Patent Number: 5,029,220

[45] Date of Patent: Jul. 2, 1991

[54] OPTICAL JOINT CORRELATOR FOR REAL-TIME IMAGE TRACKING AND RETINAL SURGERY

[75] Inventor: Richard D. Juday, Houston, Tex.

[73] Assignee: The United States of America as represented by the Administrator of the National Aeronautics and Space Administration, Washington, D.C.

[21] Appl. No.: 560,924

[22] Filed: Jul. 31, 1990

[51] Int. Cl.⁵ .................. G06K 9/00; G02B 27/42; G02B 1/12; G06E 3/00

[52] U.S. Cl. .................................. 382/6; 382/31; 382/32; 382/43; 382/49; 350/162.13; 350/3.68; 250/203.1; 244/3.17; 364/822; 606/6; 606/10; 606/18

[58] Field of Search .................. 382/31, 32, 38, 43, 382/49, 6; 350/162.12, 162.13, 162.14, 3.68, 3.82, 3.79; 364/819, 822, 826, 827; 358/105, 101, 125, 93; 351/209; 606/6, 4, 10, 17, 18; 128/395; 244/3.17; 324/77 K

[56] References Cited

U.S. PATENT DOCUMENTS

| | | | |
|---|---|---|---|
| 3,542,457 | 11/1970 | Balding | 351/7 |
| 4,357,676 | 11/1982 | Brown | 364/822 |
| 4,383,734 | 5/1983 | Huignard et al. | 350/162.13 |
| 4,438,765 | 3/1984 | Willinsky | 128/303 |
| 4,443,075 | 4/1984 | Crane | 351/209 |
| 4,462,046 | 7/1984 | Spight | 358/101 |
| 4,695,973 | 9/1987 | Yu | 364/822 |
| 4,722,101 | 9/1988 | Liu | 350/337 |
| 4,735,984 | 4/1988 | Udden et al. | 351/210 |
| 4,832,447 | 5/1989 | Javidi | 350/162.13 |
| 4,924,507 | 5/1990 | Chao et al. | 382/31 |

OTHER PUBLICATIONS

A. D. Gara, "Real-Time Tracking of Moving Objects by Optical Correlation", Applied Optics, vol. 18, No. 2, Jan. 15, 1979, pp. 172-174.

A paper by C. S. Weaver and J. W. Goodman Entitled "A Technique for Optically Convolving Two Functions", Applied Optics, vol. 5, No. 7, Jul. 1966, pp. 1248-1249.

A Paper by Bahram Javidi, Don A. Gregory & Joseph L. Horner Entitled "Single Modulator Joint Transform Correlator Architectures", Applied Optics, vol. 28, No. 3, with Printed Date of Feb. 1, 1989 (Actual Publication Date Unknown).

*Primary Examiner*—David K. Moore
*Assistant Examiner*—Michael Commarata
*Attorney, Agent, or Firm*—Hardie R. Barr; Harold W. Adams; Edward K. Fein

[57] ABSTRACT

A method for tracking an object in a sequence of images is described. Such sequence of images may, for example, be a sequence of television frames. The object in the current frame is correlated with the object in the previous frame to obtain the relative location of the object in the two frames. An optical joint transform correlator apparatus is provided to carry out the process. Such joint transform correlator apparatus forms the basis for laser eye surgical apparatus where an image of the fundus of an eyeball is stabilized and forms the basis for the correlator apparatus to track the position of the eyeball caused by involuntary movement. With knowledge of the eyeball position, a surgical laser can be precisely pointed toward a position on the retina.

7 Claims, 3 Drawing Sheets

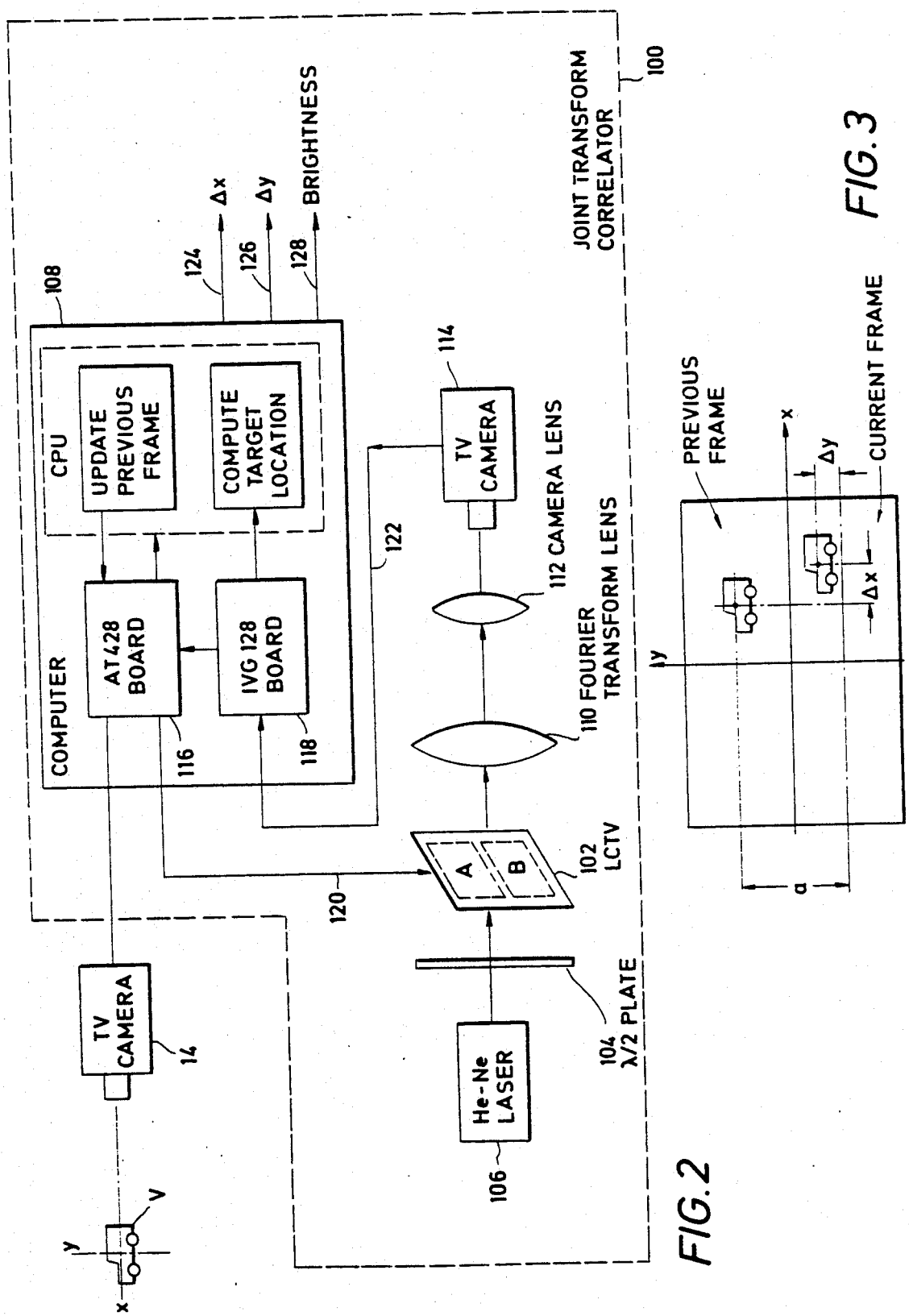

OPTICAL JOINT CORRELATOR FOR REAL-TIME IMAGE TRACKING AND RETINAL SURGERY

ORIGIN OF THE INVENTION

The invention described herein was made by an employee of the United States Government and may be manufactured and used by or for the Government of the United States of American for governmental purposes without the payment of any royalties thereon or therefor.

BACKGROUND OF THE INVENTION

1. Field of the Invention

This invention relates generally to optical correlators, and more particularly to optical correlators for real-time tracking of the position of a moving object. Still more particularly, the invention relates to a joint transform optical correlator for real-time tracking of the position of an image of the interior of the eye and, based upon such tracking directing a surgical laser beam to a precise point of the retina as directed by a surgeon.

2. Description of the Prior Art

Optical pattern recognition has been suggested in various applications because of its parallel processing and high-speed operation capabilities, particularly in real-time applications such as missile guidance, vehicle tracking, and automated lander guidance in aerospace missions. In 1974, VanderLugt in a paper entitled, "Coherent Optical Processing", Proc. IEEE 64, 1300 (1974), described the use of matched spatial filters (MSFs) in performing cloud motion analysis in a sequence of photographs taken from a satellite in half-hour intervals. A new MSF was made for every photograph in order to correlate with the scene in the next picture. Obviously such a method is not a practical real-time technique.

With the recent development of various kinds of spatial light modulators, several real-time tracking methods have been demonstrated. A. D. Gura described a liquid crystal light valve to perform real-time tracking based on a fixed MSF in a VanderLugt correlator in the paper, "Real-time tracking of moving objects by optical correlation," Appl. Opt. 18,172 (1979). T. H. Chao and H. K. Liu described a liquid crystal television spatial light modulator, a dichromated gelatin multifocus hololens and a MSF array for simultaneously tracking multiple objects in their paper, "Real-time optical holographic tracking of multiple objects," Appl. Opt. 28,266 (1989).

Optical tracking using novelty filters and image subtraction have been proposed in which the system detects the difference between sequential image frames and then computes the position of the object in motion. Such proposals are described in the paper by D. Z. Anderson, D. M. Lininger, and J. Feinberg, "Optical tracking novelty filter," Opt Lett. 12,123 (1987) and in the paper by Y. Li, A. Kostregewski, D. H. Kim, and G. Eichman, "Liquid crystal T.V.-based white light optical tracking novelty filter," Appl. Opt. 28, 4861 (1989).

The art of optical pattern recognition described above in general requires matched spatial filters that require intensive computations and individually span only a relatively small range of apperances of an object. A tracking system based on that technology thus suffers from difficulty in adapting to new objects, changes in the inherent appearance of an object, or altered perspective views of an unchanging (but moving) object.

Other methods used digital computation rather than optical filters to perform conversion from one domain to another by means of the Fourier transform. Digital computation is relatively expensive and complicated as compared to optical filtration. Furthermore it suffers from some of the same disadvantages as matched optical filtration because it has to be "taught" the pattern to be recognized on a case by case basis. Such disadvantages have prevented rapid adaptation to changes in the pattern.

Accordingly, a primary general object of the invention is to provide a method for object tracking using a joint transform correlator which does not require the use of a matched spatial filter in the correlation process.

Another general object of the invention is to provide a joint transform correlator for the tracking of a moving object which inherently includes the adaptiveness and high processing speed of an optical system.

A preferred embodiment of the optical joint correlator for image tracking according to the invention is for tracking the movement of the retinal image of an eye surgery patient.

In prior art eye surgery, nystagmic motions of the eye reduce the precision of the surgeon's aim in retinal surgery such as laser-induced photocoagulation. An eye can be paralyzed against such motions by anesthetic injection but with possible damage to the optic nerve.

Another prior art method to aim the eye surgeon's laser beam is to mount a large contact lens and attached mirrors on the eyeball. As the lens moves with the eyeball, the mirror corrects the motion of the laser beam to compensate for motion of the eyeball. The contact lens method for laser beam pointing to a particular spot on the retina is cumbersome to use and uncomfortable to the patient.

Another prior art eye surgery method is use "Purkinje" images to point a laser beam to a specific spot on the retina of an eye. Purkinje images arise from multiple reflections among surfaces near the front of the eyeball. Such method is indirect in that depends on reflections of structures near the front of the eyeball rather than being a direct image of the retina. Patients with eye disease who require eye surgery frequently also have degradation of the very structures which make the Purkinje images possible.

Accordingly, it is another object of the invention to provide a non-invasive method and apparatus for obtaining a direct image of and for precisely directing a surgeon's laser beam to a point on the retina of an eyeball.

Still another object of this invention is to provide a method and system for automatically adapting to slow changes of appearances from time frame to time frame of a tracked object, specifically a retina of an eye, which may be altered in its appearance during the progress of surgery, which may only be perspectively altered by a surgeon by changing the magnification of an optical viewing system to suit himself during the surgery.

SUMMARY

The objects identified above, as well as other advantages and features are achieved by the hybrid optical/digital system including a joint transform correlator in which an object occurring in a sequence of images is tracked. The basic idea of the invention is to provide a method and system to correlate the object in the current frame with the object in a previous frame of sequential video images so as to obtain the relative positions of the object in the two frames. The invention takes advantage of the high degree of correlation between successive appearances of an object that is changing slowly with respect to the video frame rate.

More particularly, the invention is for a method for tracking the location of a moving object which is the subject of a time sequence of video images. The image of the object is displayed in a current frame in side-by-side relation with an image of the object in some predetermined previous frame. Such previous frame may be the immediately preceding frame or a previous single reference frame which may be changed from time to time. Next, the joint display of the images is optically Fourier transformed, for example by an optical Fourier lens, to produce a joint transform power spectrum of the image of the joint display. Then, the intensity—detected joint transform power spectrum is itself encoded and optically Fourier transformed to produce a correlation function between the image of the current frame and the previous frame. The correlation function will include at least one cross-correlation peak or optical "bright spot". The intensity of such peak or spot is an indication of the degree of correlation of the object in the two images. The location of the object in the current frame is determined by updating its location in the previous frame with the location of the optical bright spot.

The joint transform correlator may be incorporated in a system for aiming a surgical laser at a point on the retina of an eye. In this specific embodiment of the invention, the retina is continuously viewed by a video camera. A frame of video is "grabbed" for subsequent use as a positional reference. Thereafter, the reference image and the real-time image are presented side-by-side in the optical joint correlator described above. A gimballed tracking mirror positioned near the eye reflects the image of the retina through a two-way mirror to the T.V. camera. A surgeon's laser beam is directed into the eye via the two-way mirror and the gimballed mirror. The "grabbed" frame of the retina is presented on a surgeon's T.V. monitor. A track ball or the like enables the surgeon to place a cross-hair or cursor or the like on the precise spot to which the laser beam is to be directed. The gimballed tracking mirror is positioned by means of track ball signals and position deviation signals from the joint transform correlator to precisely direct the laser beam to the spot identified by the surgeon on his monitor. Such correlator deviation signals track the fundus of the eye even where the eye moves during surgery.

BRIEF DESCRIPTION OF THE DRAWINGS

The objects, advantages and features of the invention will become more apparent by reference to the drawings which are appended hereto and wherein like numerals indicate like elements and wherein an illustrative embodiment of the invention is shown, of which:

FIG. 2 is a preferred embodiment of the generalized joint transform correlator according to the invention;

FIG. 3 is an illustration of the coordinate definition of an object in side-by-side display of a previous video image and a current video image.

DETAILED DESCRIPTION OF PREFERRED EMBODIMENTS

General Description of Joint Transform Correlator

Figure 1:
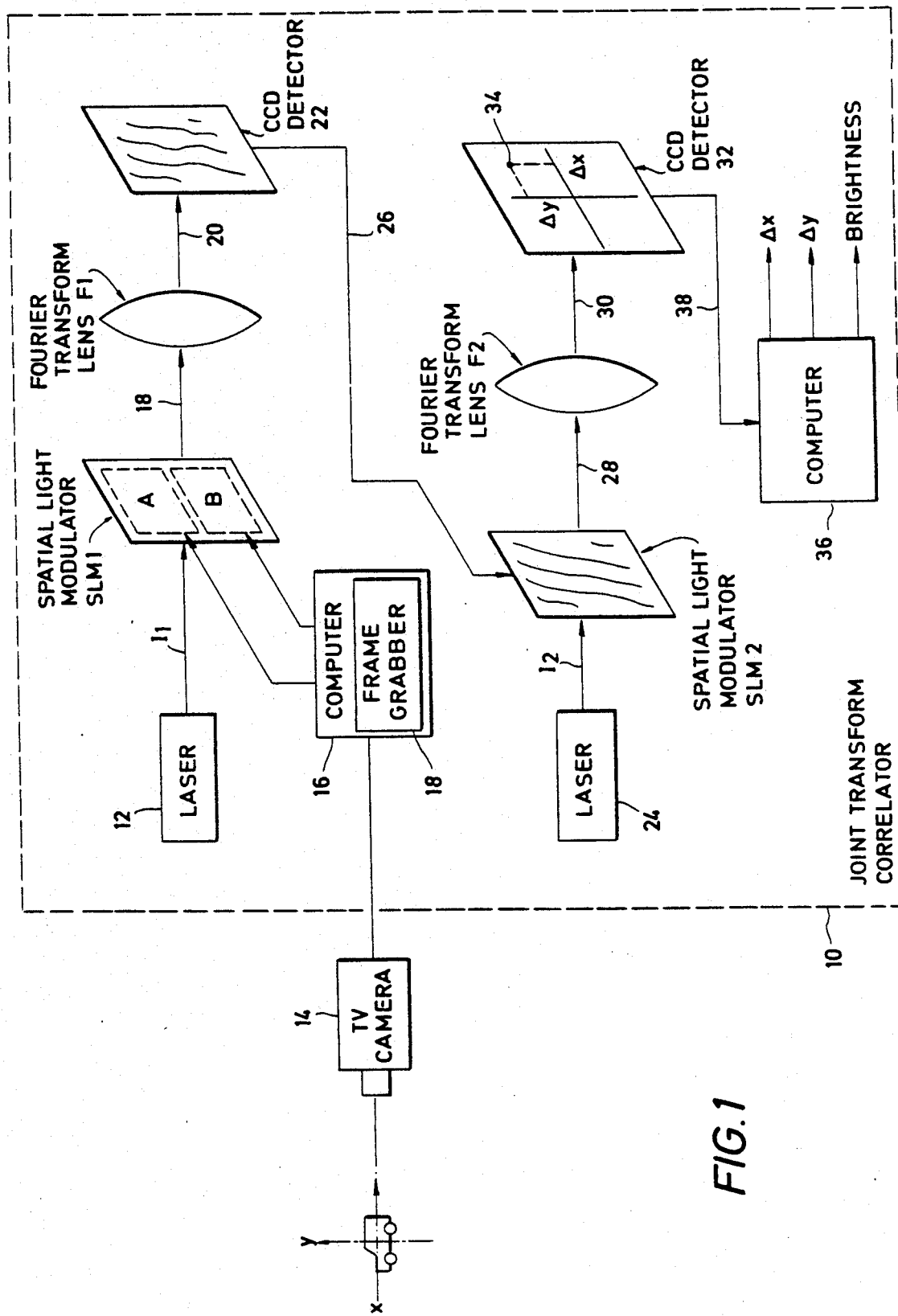
FIG. 1 is a general schematic of the method and apparatus of the invention by which the relative position of an object is tracked from frame to frame of video images of the object.

FIG. 1 illustrates the method of the joint transform correlator 10 of the invention. A laser 12 produces a coherent light beam directed toward spatial light modulator SLM1 on which images A and B are displayed. Image A is an image of an object, for example vehicle V as produced by T.V. camera 14 and as frozen by frame grabber 18 of computer 16. Image B is an image of the same object, that is vehicle V, taken at a later time. Such time may, for example, be the next available frame of the image of the object under the speed constraints of the computer 16 and other processing equipment of the system.

The beam $I_1$, through the spatial light modulator SLM1 is directed along optical path 18 through Fourier transform lens F1 which optically Fourier transforms the joint images to an optical image which is applied via optical path 20 to a CCD detector 22. The detected pattern of CCD detector 22 is written via electrical connector 26 onto spatial light modulator SLM2. The pattern of spatial light modulator is illuminated by coherent light beam $I_2$ from laser 24. The resulting beam along path 28 is applied to Fourier transform lens F2 which optically transforms the beam via path 30 to CCD detector 32. One or more bright spots or correlation peaks 34 appear on the CCD detector 32. The displacement of such spot 34 as measured by computer 36 via electrical connection 38 is representative of the amount of movement in x and y of object V from the time of frame A to frame B. The brightness or intensity of spot 34 is representative of the degree of correlation of the object appearing in the image of frame A with that in the image of frame B.

The joint transform correlator 10 may include SLM1 and SLM2 of the magneto-optic device type manufactured by Litton-Semetex. Alternatively, SLM1 and SLM2 may be deformable mirror devices manufactured by Texas Instruments. CCD Detectors 22 and 32 may be conventional CCD detectors. Fourier transform lenses F1 and F2 are conventional lens and computers 16 and 36 may be conventional micro-computers.

As indicated above, the side-by-side images presented to electrically addressed spatial light modulator SLM of FIG. 1 may be an electronic video signal. The image in the video signal may be time varying. The SLM needs to be addressable at a sufficiently high speed to resolve the movement of the object in the image. The addressing of the SLM may be optical, in which case a live optical image is presented to one half of the SLM and a static optical image is presented to the other half. Alternatively, if the SLM is electrically addressed, then the source of the electrical image (ordinary a CCD camera) must also have a sufficiently high speed to resolve the movement of the object in the image. SLM's have different speeds at which they can be addressed. The liquid crystal display of some TV's is limited to approximately 30 Hz, but ferroelectric liquid crystal material may be addressed at speeds up to tens of KHz.

Tracking by correlating a frame to a temporally immediately adjacent frame may be expected to produce the most precise results, as such pairs of images most closely resemble each other and the correlation spots will be most clearly defined. However, in that system, any measurement bias in determining the location of the correlation spot adds linearly with the number of correlated frames. The tracking will drift linearly in time with a speed given by the single-measurement bias divided by the frame rate. Such drift rate can be reduced by maintaining one master frame as the reference as long as it continues to produce a useable correlation with the tracked object. In that case the bias-induced drift rate is reduced by a factor equal to the number of frames for which the same master reference frame is used.

Preferred Embodiment of Joint Transform Correlator

The joint transform correlator 100 of FIG. 2 is a preferred embodiment of correlator 10 of FIG. 1. In this embodiment, a single spatial light modulator LCTV is used in combination with T.V. camera 14 in a feedback architecture. In this preferred embodiment a Seiko color LCTV model LVD 202, 220×240 pixels, is used with the diffuser and protective glass removed. The liquid crystal display of the commercial LCTV 102 is first removed. To compensate for the phase distortion, the liquid crystal display is then separated from the hardware circuit box and immersed in a liquid gate filled with mineral oil. The two original polarizers attached to the display unit are left untouched. A half-wave plate 104 is inserted in front of a He-Ne laser 106 to align the plane of polarization of the linear polarized light with the LCTV 102 front polarizer. These modifications are made to the Seiko LCTV model LVD 202 to obtain maximum transmission and a high constant ratio.

Two sequential scenes A and B of a moving object V are displayed on the LCTV 102 via a frame grabber of computer 108 and TV camera 14. The scenes A and B are illustrated as positioned in the upper and lower half of the LCD of LCTV 102, but of course, they may be displayed side-by-side, that is, to the right and left of each other.

The image function as illustrated in FIG. 3 illustrate that the object of the previous frame has moved an amount Delta x and Delta y in the current frame. Mathematically the image functions of the objects displayed on the LCD of LCTV 102 are $$f_{t-1}(x - x_{t-1}, y - y_{t-1} - a)_2, \text{ and}$$

$$f_t(x - x_{t-1} - \delta x, y - y_{t-1} - \delta y + a)_2$$

where $2a$ is the height of the display unit, t and t−1 are the current and previous frames, and (x, y) is the relative translation of the object from the (t−1)th to the t th frame. The complex light field at the frequency plane of Fourier Transform lens 110 may be expressed as, $$T(u,v) = F_{t-1}(u,v)\exp\{-i2\pi[ux_{t-1} + v(y_{t-1} + a)_2]\} +$$
$$F_t(u,v)\exp\{-i2\pi[u(x_{t-1} + \delta x) + v(y_{t-1} + \delta y - a)_2]\}$$

The power spectrum is magnified by lens 112 and recorded by TV camera 114 (preferably a Sony CCD camera) and then applied to computer 108, where it is grabbed and reapplied to LCTV 102. The power spectrum is thus again Fourier transformed. The complex light field at the output plane at camera lens 112 becomes, $$\begin{aligned}
C(x,y) &= F^{-1}\{|T(u,v)|^2\} \\
&= R_{t,t}(x,y) + R_{t-1,t-1}(x,y) + \\
&\quad R_{t,t-1}(x + \delta x, y + \delta y - a) + \\
&\quad R_{t-1,t}(x - \delta x, y - \delta y + a)
\end{aligned}$$

where $$\begin{aligned}
R_{m,n}(x,y) &= F^{-1}\{F_m(u,v) F_n^*(u,v)\} \\
&= \int_{-\infty}^{\infty}\int_{-\infty}^{\infty} f_m(u,v) f_n^*(u - x, v - y) du dv
\end{aligned}$$

is the correlation function between $f_m$ and $f_n$, $F^{-1}\{\cdot\}$ denotes the inverse Fourier transform of the function $\{\cdot\}$. The first two terms of the C(x,y) function above represent the zero-order terms diffracted around the origin of the output plane. The last two terms represent the cross-correlation terms diffracted at $$x_{peak1} = \delta x, \ y_{peak1} = (\delta y - a);$$

$$x_{peak2} = \delta x, \ y_{peak2} = (-\delta y + a).$$

If the object's appearance changes slowly compared with the processing cycle of the joint transform correlator, $f_{t-1}$ will strongly correlate with $f_t$, and two high-intensity correlation peaks can be observed at the output plane. The new location of the object at time t is then produced by $$x_t = (x_{t-1} + x_{peak1}) = (x_{t-1} + \delta x)$$

$$y_t = (y_{t-1} + y_{peak1} + a) = (y_{t-1} + \delta y)$$

In a preferred embodiment, camera lens 112 is a 50 mm lens used to magnify the Fourier spectrum to about 5 to 10 lines/mm. A small circular opaque dot with a blurred edge is inserted at the Fourier plane to block the D. C. light from camera 114 which would otherwise cause multiple reflections and scattering at the surface of camera 114.

The adaptive correlation method as described above requires the location of the object be initialized in the first frame. This is done by using the system with a prestored reference image located at a fixed position on LCTV 102.

An object, such as vehicle V, may have distortion variations due to variations in size, rotation orientation, and perspective. Therefore, a hierarchy search of the object may be needed. To speed the searching process, distortion invariant filters such as cicular harmonic expansion filters or synthetic discriminant function filters can be employed.

The hybrid system of FIG. 2 is controlled by a C language computer program. Computer 108 is an IBM AT compatible micro-computer which runs at 10 MHz cpu clock speed. Two video frame grabber 116, 118 are employed: the IVG 128 and AT 428 from Datacube, Inc. Such frame grabbers can digitize a full frame of input video signal into a 384 ×512 image array.

The video input of the AT 428 board 116 is connected to a Fairchild CCD TV camera 14 which is aimed at the object of interest V. The video output array of the AT 428 board 116 is applied via conduit 120 to LCTV 102. Camera 114 is connected to IVG 128 board 118 via conduit 122. Camera 114 as explained above captures the joint transform power spectrum during the first half of the processing cycle.

The recorded spectrum is sent from IVG board 128 to the AT board 116 before it can be displayed on the LCTV 102. During the second half-cycle, the correlation result is captured by camera 114 and the peak location is determined sequentially by scanning the image array for the pixel with maximum intensity. Computer 108 produces signals representative of the change in position $\delta x$, $\delta y$ of the object V and the level of brightness of the correlation peak on leads 124, 126, 128.

Application of Joint Transform Correlator in an Eye-Position Compensator

Figure 4:
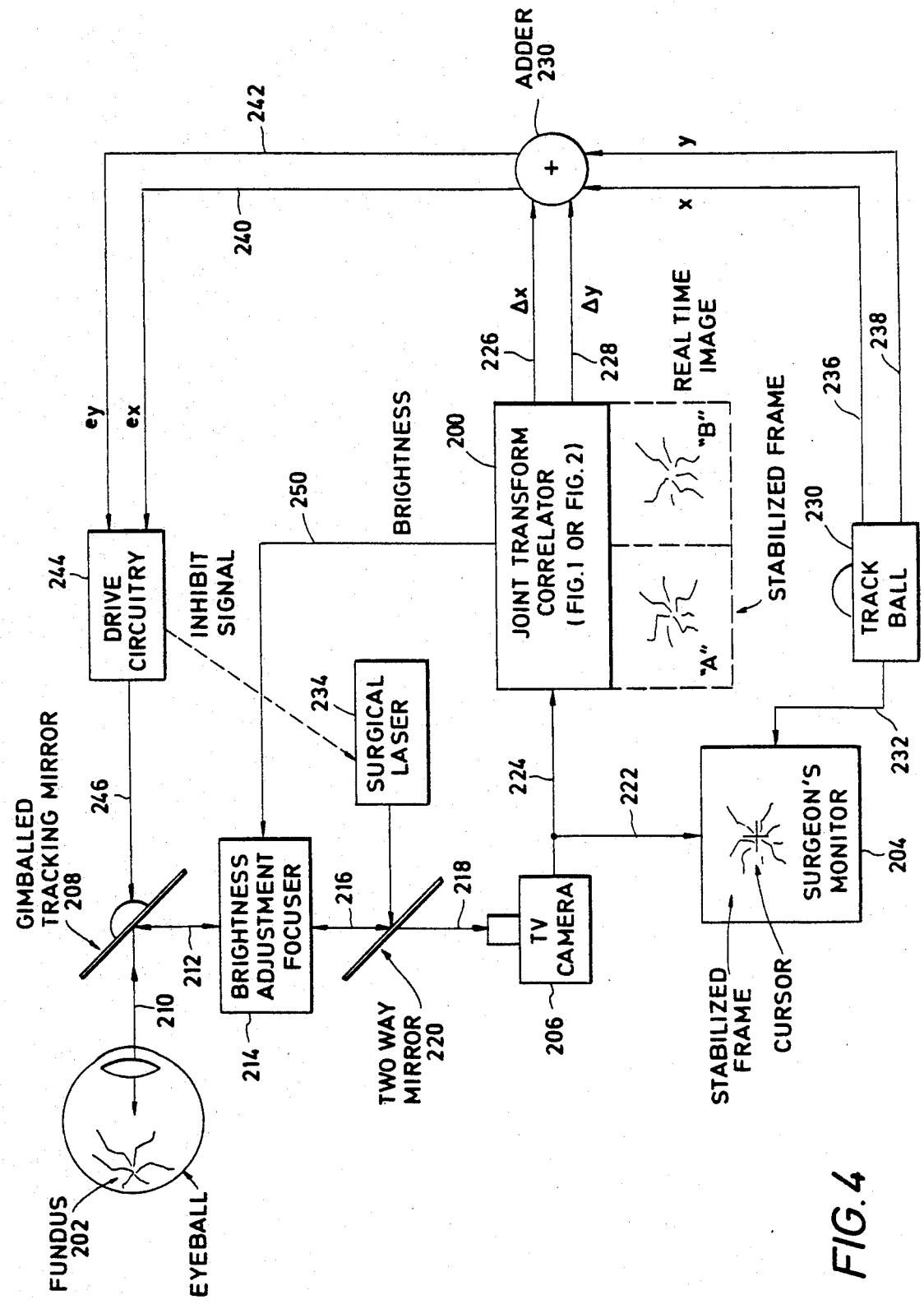
FIG. 4 is a schematic of eye surgery apparatus by which a surgeon's laser beam is precisely directed in real-time to a spot on the retina of an eye under control of a joint transform correlator even where the patient's eye is moving.

FIG. 4 illustrates a preferred application in the field of eye surgery of the joint transform correlator described above. A joint transform correlator 200 is illustrated schematically, and, of course, may be physically realized as in FIG. 2.

An eye's retina image or fundus is displayed on a surgeons monitor 204 via the captured image of it by TV camera 206 viewing it via gimballed tracking mirror 208. The image path of the fundus 202 is applied via path 210 to mirror 208 and thence via path 212 to brightness adjustment mechanism 214 and then via path 216 to two-way mirror 220 and path 218 to TV camera 206. The fundus image is applied to monitor 204 as a stabilized or "frozen" frame via conduit 222 and is also applied to Joint Transform Correlator 200 via conduit 224. It is applied on one side of the pattern to be jointly transformed, while subsequent images of the fundus are applied on the other side. The joint transform correlator produces "delta" output signals $\delta x$, $\delta y$ representative of the amount of movement in the x and y direction that the fundus image has moved with respect to the image of the frozen frame. Such $\delta x$ and $\delta y$ signals are applied on leads 226 and 228 to an adder 230 and ultimately applied to gimballed tracking mirror 208 for bringing the real-time image of the fundus into correspondence with the frozen frame image.

A track ball 230 is connected to monitor 204 via lead 232 to enable the surgeon to precisely fix a curser or cross-hair onto a position of the fundus 202 at which laser beam from laser 234 is to be directed. Output signals x and y from leads 236 and 238 are applied to adder 230 where they are respectively added to the $\delta x$ and $\delta y$ signals on leads 226 and 228. The error signals $e_x$ and $e_y$ on leads 240 and 242 are applied to drive circuitry 244. As a result, link 246 turns gimballed tracking mirror to precisely point the laser beam from laser 234 and two-way mirror toward the cross-trained point of fundus 202.

The real-time image B of the fundus is driven into coincidence with the grabbed frame image A, thereby stabilizing the virtual position of the retina. With modern micro-computers and equipment depicted in FIG. 4, a correlation measurement can be performed in 4 m sec whereas the highest frequencies in nystagmic eye motion is 150 Hz (or a period of approximately 7 m sec). Accordingly the surgeon's monitor is presented with a stabilized image of the eye's fundus.

The brightness adjustment focus mechanism 214 receives brightness signal on lead 250 from joint transform correlator 250. The level of such signal, which represents the degree of correlation between the real-time image B and the frozen frame image A, adjusts the focus and accordingly the spread of the laser beam as it is applied to the fundus. The better the correlation between the frozen frame image A and the real-time image B, the sharper the focus of the laser beam applied to the retina. The tracking system is thus able to compensate for involuntary changes in focus of the patient's eye and thus minimize the size of the spot the laser strikes on the retina. Loss of correlation spot brightness below a predetermined threshold may be used to prevent the laser beam from being transmitted to the eye and may be used to signal the surgeon that a new master or frozen frame of the retina is required before further processing can proceed.

The dynamic position of the correlation spot as measured by signals $e_x$, $e_y$ to drive circuitry 244 may be used to inhibit the operation of surgical laser 234. If the eyeball twitches out of position, the joint transform correlator 200 can sense such condition faster than a surgeon and can inhibit operation to laser 234 if signals $e_x$, $e_y$ are greater than a predetermined threshold value. Drive circuitry 244 includes threshold circuitry for comparing signals $e_x$ and $e_y$ against predetermined threshold values. Such feature of the apparatus of FIG. 4 is advantageous in that a surgeon is enabled to work closer to the retina's fovea with the knowledge that the apparatus will inhibit the laser's firing if the eye movement has been so fast and so large that the system has not been able to compensate for it at the moment the laser would otherwise fire.

Various modifications and alterations in the described methods and apparatus will be apparent to those skilled in the art of the foregoing description which does not depart from the spirit of the invention.

Eye surgery is only one specific example of the tracking technique invention disclosed above. Another application is to replace mechanical gyroscopes which stabilize a tape recorded video from a hand-held video camera. In such an application, the gross scene changes only a small amount from frame to frame. The jitter from frame to frame is caused principally by the motion of the person holding the camera. With the invention described above, such motion is measured and then electronically compensated by electronic offset addressing during storage or by re-aiming the lens. Such apparatus and method eliminates the need for the mechanical gyroscope.

Accordingly such applications as described are included in the scope of the appended claims. The appended claims recite the only limitation to the present invention. The descriptive manner which is employed for setting forth the embodiments should be interpreted as illustrative but not limitative.

What is claimed is:

1. A method for tracking the position of an object in a time sequence of time-sampled images of the object comprising the steps of,
    displaying sequential contiguous images of said object in side-by-side relation on a first spatial light modulator to produce a first SLM image,
    illuminating said first SLM image with a coherent light beam to produce a first modulated beam,
    optically Fourier transforming said first modulated beam to produce a transformed optical image of said side-by-side images,
    detecting said transformed optical image to produce a first detected display of said transformed side-by-side images, displaying said first detected display on a second spatial light modulator to produce a second SLM image, illuminating said second SLM image with a coherent light beam to produce a second modulated beam, optically Fourier transforming said second modulated beam to produce a correlation optical beam of said side-by-side images, detecting said correlation optical beam to produce a correlation image of light spots representative of the joint correlation of said two images, measuring the translational relationship between said light spots to determine the positional relationship of said object between said two images, and periodically repeating the above steps with the sequence of time-frozen images being displayed in time sequence in side-by-side relationship on said first spatial light modulator.

2. The method of claim 1 further comprising the step of measuring the brightness of said light spots of said correlation image to determine the degree of resemblance of said two images.

3. A method for tracking the location of a moving object in a time sequence of video images comprising the steps of, displaying an image of said object of the current frame in side-by-side relation with an image of said object in a previous contiguous frame to produce a joint display of said images, optically Fourier transforming said joint display of said image to produce a joint transform power spectrum of the image of said joint display, optically Fourier transforming said joint transform power spectrum to produce a correlation function between said image of said current frame and said image of said previous frame, said correlation function including at least one cross-correlation peak, and determining the location of said object in said current frame by updating its location in said previous frame with the location of said cross-correlation peak.

4. Apparatus for tracking the position of an object appearing in a sequence of contiguous time-frozen images of the object comprising, a first spatial light modulator, means for displaying said contiguous images of said object in side-by-side relation on said first spatial light modulator to produce a first SLM image, means for illuminating said first SLM image with a coherent light beam to produce a first modulated beam, Fourier lens means for transforming said first modulated beam to produce a Fourier transformed optical image of said side-by-side images, means for detecting said transformed optical image to produce a first detected display of said transformed side-by-side images, a second spatial light modulator, means for displaying said second detected display on said second spatial light modulator to produce a second SLM image, means for illuminating said second SLM image with a coherent light beam to produce a second modulated beam, means for optically Fourier transforming said second modulated beam to produce a correlation optical image of said side-by-side images, and means for detecting said correlation optical beam to produce a correlation image of light spots representative of the joint correlation of said two images, and means for measuring the position of at least one of said light spots as a measure of the position between said object in said two images.

5. Apparatus for aiming a surgical laser at a point in the interior of an eye comprising, gimballed tracking mirror means positioned near said eye for reflecting an optical image of the interior of said eye, surgical laser means for generating a surgical light beam, two way mirror means disposed in the path of said optical image of the interior of said eye and in the path of said surgical light beam for passing said optical image through said two way mirror and for reflecting said surgical light beam to said gimballed tracking mirror, camera means in the path of said optical image from said two way mirror means for generating an electronic image signal representative of the interior of said eye, a surgeon's TV monitor means responsive to said electronic image signal for displaying a stabilized frame image of said image of the interior of said eye, positioning means for moving a cursor to a particular point on said TV monitor so as to coincide with an aim point on said stabilized frame image of the interior of said eye and for producing x and y signals representative of the x and y locations of said cursor, joint transform correlator means responsive to said electronic image signal representative of the interior of said eye including, means for displaying said stabilized frame image of the interior of said eye on one side of a joint display and for sequentially frames of said image on another side of said joint display, means for sequentially optically producing a display of the correlation function between said side-by-side images, and means for determining the location of each sequential image with respect to said image of said stabilized frame and for producing $\delta x$ and $\delta y$ signals representative of the location of at least one cross-correlation peak, said $\delta x$ and $\delta y$ signals representative of the movement of said image with respect to said image of said stabilized frame, adder means for adding said x signal and said $\delta x$ signal to produce an error x signal and for adding said y signal and said $\delta y$ signal to produce an error y signal, and drive circuitry means responsive to said error x and error y signals for positioning said gimballed tracking mirror means so that said surgical laser beam is pointed to said cursor point of said stabilized frame image of the eye independent of motion of said eyeball.

6. The apparatus of claim 5 wherein said joint transform correlator means further produces a brightness signal representative of the brightness of said cross-correlation peak and said apparatus further comprises, dynamic adjustment means responsive to said brightness signal for controlling said surgical light beam as a function of the degree of correlation between said image of said stabilized frame of said eye and said real-time image of said eye.

7. The apparatus of claim 5 further comprising,
means for inhibiting the firing of said surgical laser means if said error x and error y signals are greater than predetermined threshold values.

* * * * *